US008623409B1

(12) United States Patent
Mehta et al.

(10) Patent No.: US 8,623,409 B1
(45) Date of Patent: Jan. 7, 2014

(54) CLONIDINE FORMULATION

(75) Inventors: Ketan Mehta, Cranbury, NJ (US); Yu-Hsing Tu, West Windsor, NJ (US)

(73) Assignee: Tris Pharma Inc., Monmouth Junction, NJ (US)

(*) Notice: Subject to any disclaimer, the term of this patent is extended or adjusted under 35 U.S.C. 154(b) by 323 days.

(21) Appl. No.: 12/908,796

(22) Filed: Oct. 20, 2010

(51) Int. Cl.
*A61K 9/22* (2006.01)
*A61K 9/20* (2006.01)
*A61K 9/28* (2006.01)
*A61K 9/14* (2006.01)
*A61K 31/415* (2006.01)
*A01N 43/52* (2006.01)
*A01N 33/18* (2006.01)
*A01N 33/24* (2006.01)
*A61K 31/04* (2006.01)

(52) U.S. Cl.
USPC ........... 424/468; 424/464; 424/474; 424/483; 424/484; 424/487; 514/388; 514/740; 514/965; 514/964

(58) Field of Classification Search
USPC ................ 424/464, 468, 474, 483, 484, 487; 514/388, 740, 964, 965
See application file for complete search history.

(56) References Cited

U.S. PATENT DOCUMENTS

| 4,201,211 A | 5/1980 | Chandrasekaran |
| 4,221,778 A | 9/1980 | Raghunathan |
| 4,603,141 A | 7/1986 | Giles |
| 4,762,709 A | 8/1988 | Sheumaker |
| 4,792,450 A | 12/1988 | Kydonieus |
| 4,996,047 A | 2/1991 | Kelleher |
| 5,133,974 A | 7/1992 | Padadissis |
| 5,273,760 A | 12/1993 | Oshlack et al. |
| 5,275,820 A | 1/1994 | Chang |
| 5,286,493 A | 2/1994 | Oshlack et al. |
| 5,288,497 A | 2/1994 | Stanley et al. |
| 5,296,228 A | 3/1994 | Chang et al. |
| 5,484,607 A | 1/1996 | Horacek |
| 5,580,578 A | 12/1996 | Oshlack et al. |
| 5,869,100 A | 2/1999 | Horacek |
| 5,874,090 A | 2/1999 | Baker |
| 5,958,458 A | 9/1999 | Nortling et al. |
| 5,968,551 A | 10/1999 | Oshlack et al. |
| 5,980,882 A | 11/1999 | Eichman |
| 6,001,392 A | 12/1999 | Wen et al. |
| 6,030,642 A | 2/2000 | Horacek |
| 6,046,277 A | 4/2000 | Kolter et al. |
| 6,066,334 A | 5/2000 | Kolter et al. |
| 6,096,339 A | 8/2000 | Ayer et al. |
| 6,228,863 B1 | 5/2001 | Palermo et al. |
| 6,231,936 B1 | 5/2001 | Kozimor |
| 6,326,027 B1 | 12/2001 | Miller et al. |
| 6,432,440 B1 | 8/2002 | Watts |
| 6,500,459 B1 | 12/2002 | Chhabra et al. |
| 6,627,635 B2 | 9/2003 | Palermo et al. |
| 6,696,088 B2 | 2/2004 | Oshlack et al. |
| 6,960,357 B2 | 11/2005 | Chopra |
| 7,067,116 B1 | 6/2006 | Bess et al. |
| 7,070,806 B2 | 7/2006 | Oshlack et al. |
| 7,125,563 B2 | 10/2006 | Kumbhani et al. |
| 7,144,587 B2 | 12/2006 | Oshlack et al. |
| 7,153,497 B2 | 12/2006 | Hughes et al. |
| 7,611,730 B2 | 11/2009 | Bartholomaus et al. |
| 7,884,122 B2 | 2/2011 | Hornacek et al. |
| 8,062,667 B2 | 11/2011 | Mehta |
| 2002/0132001 A1 | 9/2002 | Garthwaite et al. |
| 2002/0156133 A1 | 10/2002 | Bartholamaeus |
| 2003/0004177 A1 | 1/2003 | Kao et al. |
| 2003/0050620 A1 | 3/2003 | Odidi et al. |
| 2003/0082230 A1 | 5/2003 | Baichwal et al. |
| 2003/0099711 A1 | 5/2003 | Meadows et al. |
| 2004/0022852 A1 | 2/2004 | Chopra |
| 2004/0062802 A1 | 4/2004 | Hermelin |
| 2004/0096501 A1 | 5/2004 | Vaya |
| 2004/0126428 A1 | 7/2004 | Hughes |
| 2004/0170684 A1 | 9/2004 | Baichwal et al. |
| 2005/0112201 A1 | 5/2005 | Baichwal et al. |
| 2005/0118267 A1 | 6/2005 | Baichwal et al. |
| 2005/0142097 A1 | 6/2005 | Thassu et al. |

(Continued)

FOREIGN PATENT DOCUMENTS

JP  62048618  3/1987
JP  H02-172912 A  7/1990

(Continued)

OTHER PUBLICATIONS

Boehringer Ingelheim, "Catapres®" Prescribing Information/Product Insert, Apr. 2010.
Sciele Pharma, Inc., News Release, "Sciele Pharma and Addrenex Announce Initiation of Pivotal Phase III Trials for Clonicel for ADHD", Oct. 30, 2007.
"Clonidine Extended Release (ER) Oral Suspension", FDA-Approved Product Literature, Rev 00, Nov. 2009.
"Nexidon XR (Clonidine) Extended-Release Oral Suspension" FDA-Approved Product Literature, Rev 00, Aug. 2010.
"Addrenex Pharmaceuticals Reaches Milestone with Filing of NDA for First Product, CloniBID, to Treat Hypertension", Feb. 20, 2008.
Addrenex Pharmaceuticals, Inc., Press Release, "Addrenex Pharmaceuticals Announces Positive Phase III Clinical Results for Clonicel to Treat ADHD: Non-Stimulant Drug Addresses Wide Range of Symptoms of ADHD", Sep. 10, 2008.

(Continued)

*Primary Examiner* — Mina Haghighatian
*Assistant Examiner* — Helen Chui
(74) *Attorney, Agent, or Firm* — Howson & Howson LLP; Cathy A. Kodroff; Egon Berg (57) ABSTRACT

An oral clonidine dosage unit providing a twenty-four hour extended release profile following a single dose administration is provided. The dosage unit comprises a pharmaceutically effective amount of a coated complex comprising clonidine bound to a cationic exchange resin, which is characterized by a twenty-four hour release profile with a single peak, wherein said oral clonidine dosage unit provides a therapeutically effective plasma concentration for at least about 70%, or at least 85% of the twenty-four hour period following the single dose administration. Both liquid and solid formulations are provided, as are methods of treating a patient by a single administration of a formulation of the invention so as to achieve a therapeutic effect for 24-hours.

28 Claims, 2 Drawing Sheets

(56) References Cited

U.S. PATENT DOCUMENTS

| | | | |
|---|---|---|---|
| 2005/0181050 | A1 | 8/2005 | Hirsh et al. |
| 2005/0232986 | A1 | 10/2005 | Brown |
| 2005/0232987 | A1 | 10/2005 | Brown et al. |
| 2005/0265955 | A1 | 12/2005 | Raman et al. |
| 2005/0266032 | A1 | 12/2005 | Srinivasan |
| 2006/0024368 | A1 | 2/2006 | Fassihi et al. |
| 2006/0029664 | A1 | 2/2006 | Srinivasan |
| 2006/0057205 | A1 | 3/2006 | Srinivasan |
| 2006/0062838 | A1 | 3/2006 | DiPierro et al. |
| 2006/0134148 | A1 | 6/2006 | Hollenbeck |
| 2006/0134207 | A1 | 6/2006 | Srinivasan |
| 2006/0204587 | A1 | 9/2006 | Kolter |
| 2006/0263431 | A1 | 11/2006 | Maloney |
| 2006/0286174 | A1 | 12/2006 | Raman |
| 2007/0003512 | A1 | 1/2007 | Stockel et al. |
| 2007/0092553 | A1 | 4/2007 | Tengler |
| 2007/0215511 | A1 | 9/2007 | Mehta |
| 2007/0218140 | A1 | 9/2007 | Tanabe et al. |
| 2008/0152709 | A1 | 6/2008 | Bortz |
| 2008/0175910 | A1 | 7/2008 | Andre et al. |
| 2009/0047345 | A9 | 2/2009 | Lenaerts et al. |
| 2009/0264490 | A1 | 10/2009 | Zanella et al. |
| 2010/0166858 | A1 | 7/2010 | Mehta et al. |
| 2012/0015030 | A1 | 1/2012 | Mehta et al. |

FOREIGN PATENT DOCUMENTS

| | | | |
|---|---|---|---|
| JP | H05-279247 | A | 10/1993 |
| JP | 2003-528910 | A | 9/2003 |
| JP | 2005-306778 | A | 11/2005 |
| WO | WO 03/020242 | A1 | 3/2003 |
| WO | WO 2004/067039 | A1 | 8/2004 |
| WO | WO 2005/117843 | A2 | 12/2005 |
| WO | WO 2006/101536 | A1 | 9/2006 |

OTHER PUBLICATIONS

TrisPharma, Press Release, "Tris Pharma announces Two NDA Approvals from FDA Including a Pioneering, First-Ever 24 Hour Liquid Sustained Release Product", Dec. 7, 2009.

Seong Hoong Jeong, Development of Sustained Release Fast-melting Tablets Using Ion Exchange Resin Complexes Dissertations, Submitted to Purdue University, W. Lafayette, Indiana, pp. 92-105, 114, 141, 142,169, UMI #3210729, (Dec. 2005).

Seong Hoong Jeong, "Evaluation of Drug Release Properties from Polymer Coated Drug/Ion-Exchange Resin Complexes Using Mathematical Simulation and Their Application into Sustained Oral Drug Delivery", Department of Pharmaceutical Chemistry, University of Kansas, Abstract, (Jun. 16-18, 2005).

Quadir, Anisul, FDA Excipient Workshop, "Development of High Functionality Excipients for Immediate and Sustained Release Dosage Forms", (Sep. 20, 2004).

Shao et al, Effects of Formulation Variables and Post-Compression Curing on Drug Release from a New Sustained-Release Matrix Material: Polyvinylacetate-Povidone, Pharmaceutical Development and Technology, 6(2):247-254, (2001).

Shao et al, "Drug Release from Kollicoat SR30D-Coated Nonpareil Beads: Evaluation of Coating Level, Plasticizer Type, and Curing Condition", AAPS PharmSciTech (Feb. 12, 2002); vol. 3 (Issue 2), article 15 (http://ww.aapspharmascitech.org).

Nissen et al, Solid Medication Dosage Form Modification at the Bedside and in the Pharmacy of Queensland Hospitals, Journal of Pharmacy Practice and Research, 39(2):129, (Apr. 2009).

Glass, B. and Haywood, A., Stability Consideration in Liquid Dosage Forms Extemporaneously Prepared from Commercially Available Products, Journal of Pharmacy & Pharmaceutical Sciences, 9(3):398-426, (Dec. 2006).

U.S. Appl. No. 12/261,349, filed Oct. 30, 2008, for "Scalable Process for Manufacture of Resin Complexes for Pharmaceutical Use", Mehta, et al.

U.S. Appl. No. 13/457,646, filed Apr. 27, 2012, for "Method for Preparing Liquid Suspensions Containing Coated Drug—Ion Exchange Resin Complexes", Mehta, et al.

U.S. Appl. No. 12/261,349, filed Oct. 20, 2006, Mehta, et al.

U.S. Appl. No. 13/457,646, filed Apr. 27, 2007, Mehta, et al.

U.S. Appl. No. 13/244,706, filed Sep. 26, 2011, Mehta, et al.

Office Action issued in counterpart JP Patent Application No. 2009-500494, with translation of Notice of Reasons for Rejection, bibliography from official gazettes, and excerpts of four "references".

Brickman et al., Circadian variations of catecholamines and blood pressure in patients with pseudohypoparathyroidism and hypertension. Chronobiologia, Jan.-Mar. 1990, vol. 17(1):37-44 (Abstract Only).

Carter, JC "The Role of Lubricants in Solid Oral Dosage Manufacturing" (2006), [retrieved on Apr. 16, 2010] Retrieved from the Internet: URL:http://www.carterpharmaceuticalconsulting.com/articles/role-of-lubricants-in-solid-dosage-manufacturing.html.

Ettmayer et al, Lessons learned from marketed and investigational prodrugs. Journal of Medicinal Chemistry, May 2004 vol. 47(10):2393-2404.

Flaa and Kjeldsen, Are all hypertensives made equal? Herz, Jun. 2006, vol. 4:323-330.

Fyhrquist F, Comparison of sustained-release and standard preparations of clonidine in essential hypertension, International Journal of Clinical Pharmacology, Therapy, and Toxicology, Dec. 1983, 21(12):634-6.

Gerber et al., Antihypertensive pharmacology. The Western Journal of Medicine, May 1980, vol. 132:430-439.

Hajjar and Kotchen,. Trends in prevalence, awareness, treatment, and control of hypertension in the United States, JAMA, Jul. 2003 vol. 290(2): 199-206.

Hermida et al., Administration-time-dependent effects of hypertensive treatment on the circadian pattern of blood pressure. Current Opinion in Nephrology and Hypertension, Sep. 2005, vol. 14:453-459.

MacGregor et al., Pharmacokinetics of oral sustained release clonidine in humans, Arzneimittelforschung, 1985, 35(1A):440-6.

Martens et al, A clinical study on the prolonged antihypertensive effect of clonidine in a sustained-release capsule formulation, Pharmatherapeutica, 1980; 2(7): 456-61.

Prisant et al., Novel drug-delivery systems for hypertension, The American Journal of Medicine, Aug. 1992, 93(2a):455-555.

Product Literature, KAPVAY (clonidine hydrochloride) extended-release tablets, oral, 2010.

Product Literature, NEXICLON™ XR (clonidine) Extended-Release Oral Suspension, Aug. 2010.

Product Literature, NEXICLON™ XR (clonidine) Extended-Release Tablets, Aug. 2010.

Schook et al., Overview of clinical trials with urapidil, The American Journal of Cardiology, Aug. 1989, 64(7): 30D-37D.

ScienceLab.com, "Material Safety Data Sheet: Clonidine HCl" (2008) [Retrieved on Apr. 16, 20120]. Retrieved from the Internet: URL :http/www.sicencelab.com/xMSDS-Clonidine_Hcl-9923511.

Steger, Treatment of hypertensive out-patients with a sustained-release dosage form of clonidine: a comparison with standard tablet therapy and long-term follow-up study. Current Medical Research and Opinion., 1980, vol. 6:670-676.

Testa B. Prodrug research: Futile or fertile. Biochemical Pharmacology, Dec. 2004, vol. 68:2097-2106.

Timmermans and Van Zwieten,. Quantitative structure-activity relationships in centrally acting imidazolidines structurally related to clonidine. Journal of Medicinal Chemistry, Dec. 1977 vol. 20(12):1636-1644.

Van Zwieten, et al, Pharmacology of centrally acting hypotensive drugs, 1980 vol. 10: 13S-20S.

Wolf-Maier et al., Hypertension treatment and control in five European countries, Canada, and the United States. Hypertension, Jan. 2004, vol. 43:10-17.

Japanese Patent No. 61245014,applicant Teijin Ltd, published Jun. 29, 1987, (Abstract Only).

Davies et al., Pharmacokinetics and concentration-effect relationships of intervenous and oral clonidine (May 1977).

FIG. 2

CLONIDINE FORMULATION

BACKGROUND OF THE INVENTION

This invention relates generally to formulations containing clonidine, and more specifically, to a formulation providing a twenty-four hour release profile in a single daily dosage unit.

Clonidine (known chemically as N-(2,6-dichlorophenyl)-4,5-dihydro-1H-imidazol-2-amine) is characterized by the structure:

The pharmaceutical product containing the hydrochloride salt of clonidine is commercially available as Catapres® (USP from Boehringer Ingelheim Pharmaceuticals, clonidine hydrochloride or 2-(2,6-dichlorophenylamino)-2-imidazoline hydrochloride, MW 266.56). Catapres® is a centrally acting alpha-agonist hypotensive agent available in tablet form for oral administration in three dosage strengths: 0.1 mg, 0.2 mg and 0.3 mg. The 0.1 mg tablet is equivalent to 0.087 mg of the free base. Another commercial tablet is available from Dixarit. The active drug is also available as a transdermal patch (Catapres-TTS), or as an injectable form to be given epidurally, directly to the central nervous system. This drug is useful for treating a number of conditions and may also be used to ease withdrawal symptoms associated with the long-term use of narcotics, alcohol and nicotine (smoking).

Some of the side effects described for clonidine, including lightheadedness, dry mouth, dizziness, or constipation, are believed to be associated with the timing of peak plasma concentrations afforded by the current immediate release formulations. For example, current immediate release clonidine products are administered twice a day, providing two peak plasma concentrations 3-5 hours after each administration. This results in unwanted sedating effects during the day time. When administered orally, dry mouth is also associated with peak plasma concentrations.

An extended release clonidine formulation has been described in U.S. Pat. No. 5,133,974. This document describes formulations comprising a mixture of 0 to about 50% of an immediate release particle comprising a core of at least one drug and up to 100% of an extended release particle which comprises the immediate release particle additionally coated with a dissolution modifying system and optionally an additional drug. US Patent Publication No. 2008/0152709 (Jun. 26, 2009) describes a method for treating a patient with clonidine once daily in a dose of about 0.1 to about 2 mg (based on the weight of the HCl salt form). The composition is described as having a 24-hour profile of plasma clonidine concentration that does not substantially fall below about 0.2 ng/mL and does not substantially exceed about 1 ng/mL. One dosage unit is described as having (a) zero to about 50% by weight of particles of a first kind comprising clonidine and having an immediate release profile and (b) about 50% to about 100% by weight of particles of a second kind comprising clonidine and exhibiting an extended release profile. In some embodiments, this dosage form is described as having a peak plasma clonidine concentration of about 4 to about 16 hours after administration. However, the document fails to provide any detailed illustrations of how to formulate clonidine so as to achieve the described release profile.

U.S. Pat. No. 6,030,642, reports that it provides an extended release clonidine formulation in the form of a capsule, which avoids the "peak and trough" side effects of traditional oral clonidine formulations. The formulation is indicated to be a homogenous mixture of clonidine, one or more cellulose ethers, and one or more inert, pharmaceutically accepted fillers.

The binding of drugs on ion exchange particles to achieve sustained release has been described. Clonidine has been described as one drug which could be bound to such an ion exchange resin particle. See, e.g., U.S. Pat. No. 5,296,228; U.S. Pat. Nos. 5,275,820; 4,996,047. Liquid suspensions containing coated drug-ion exchange resin complexes and matrices are described in US Published Patent Application No. US-2007-0215511-A1 (Sep. 20, 2007).

There remains a need for methods for treating diseases or disorders using clonidine in a way which minimizes the side effects associated with "peak" and "trough" effects, and which provides a more efficient way of dosing. There is also a need for orally deliverable pharmaceutical compositions useful in these methods.

SUMMARY OF THE INVENTION

The present invention provides a formulation of clonidine which provides a 24-hour profile in a dosage unit which is administered once daily. Advantageously, the dosage unit may be administered prior to bedtime, so that the side effects associated with peak plasma concentration following current oral formulations occurs during the sleeping hours.

In one aspect, the invention provides an oral clonidine dosage unit having a twenty-four hour extended release profile following a single oral administration. The dosage unit comprises a pharmaceutically effective amount of a coated complex comprising clonidine bound to a cationic exchange resin, which provides having a twenty-four hour release profile with a single plasma concentration peak. This oral clonidine dosage unit provides a therapeutically effective plasma concentration for at least about 70%, or at least about 85% of the twenty-four hour period following the single oral dose. In one embodiment, the dosage unit is a solid, e.g., a tablet. In another embodiment, the dosage unit is a liquid suspension.

In another aspect, the invention provides an oral clonidine pharmaceutical composition comprising a once-a-day modified release formulation comprising a pharmaceutically effective amount of a barrier coated complex comprising clonidine bound to a cationic exchange resin which provides a mean plasma concentration in human patients of about 0.49 (±0.09) ng/mL at about 7.8 hours (±1.7 hours) following a single clonidine dose equivalent to about 0.2 mg clonidine hydrochloride.

In yet another aspect, the invention provides an oral clonidine dosage unit providing a twenty-four hour extended release profile following a single oral dose, said dosage unit comprising a pharmaceutically acceptable amount of a coated complex comprising clonidine bound to a cationic exchange resin comprising a sulfonated copolymer of styrene with divinylbenzene in a ratio of about 1:120 to about 1:180 (optionally in a matrix), and wherein the complex has a cured water-permeable, high tensile strength, water insoluble, barrier coating comprising a non-ionic polymer and a plasticizer and having an elongation factor in the range of about 150% to about 400%. In one embodiment, the dosage unit comprises a multiplicity of coated clonidine-cation exchange resin complexes, said coated complexes having an average particle size in the range of about 20 microns to about 200 microns.

In still a further aspect, the invention provides a method for delivering an effective amount of clonidine for twenty-four hours in a single oral dose. The method involves administering to a subject a single oral clonidine dosage unit as described herein.

In yet another aspect, the invention provides a method for the preparation of an oral once-daily clonidine delivery system without food effect, comprising the steps of coating a cationic exchange resin with a cured water-permeable, high tensile strength, water insoluble, barrier coating comprising polyvinylacetate, and a plasticizer, said barrier coating having an elongation factor in the range of about 150% to 400%; and mixing clonidine hydrochloride and the cation exchange resin in a weight ratio of about 1:120 to about 1:180 under conditions which permit the clonidine to form a complex with the cation exchange resin.

These and other advantages of the present invention will be readily apparent from the following detailed description of the invention.

DETAILED DESCRIPTION OF THE INVENTION

The present invention provides a clonidine formulation which delivers a 24-hour release effective plasma profile which exhibits no food effect. Due to the prolongation of the drug release of up to about 24 hours, compositions of the present invention are useful because the once-a-day dose provides a more consistent supply (release) of the clonidine to patients who otherwise may have to be take multiple doses a day, thereby exposing those patients to multiple peaks of the drug and unwanted side effects associated with such multiple peaks. In one embodiment, the invention provides a multiparticulate homogeneous suspension system. This is especially beneficial in the case of small children, elderly people, or others, who have difficulty swallowing larger solid dosage forms such as tablets or capsules. In another embodiment, the invention provides a tablet formulation.

As used herein, the ten "modified release" refers to compositions which are characterized by having at least one of the active components having a release over a period of at least about 6 to about 8 hours, and up to 24-hours. The term "modified release" may include, e.g., compositions which are extended release formulations, sustained release formulations, or delayed release formulations. The release profile may be assessed using in vitro dissolution assays known to those of skill in the art [e.g., USP basket method or Paddle Method, or channel flow method]. The release profile can be assessed in vivo (e.g., for bioavailability determinations), using plasma concentrations to assess maximum concentration ($C_{max}$) and area under the curve (AUC). Such assays are well known to those of skill in the art.

"$C_{max}$" is the maximum observed plasma concentration, calculated as the mean of the individual maximum blood plasma concentrations.

The term "mean maximum plasma concentration" (mean $C_{max}$) is defined for the purposes of the present invention as the maximum mean plasma concentration.

"Mean plasma concentration" is the arithmetic mean blood plasma concentration.

The term "$t_{max}$" is the time at which $C_{max}$ is achieved.

The term "$T_{max}$" is the time at which the maximum blood plasma concentration is observed for each individual participating in the bioavailability study.

$AUC_{last}$ is the mean area under the plasma concentration-time curve from time 0 to the last with quantifiable concentration. This may be calculated using the log-linear trapezoidal rule that means linear trapezoidal rule up to Tmax, and log trapezoidal rule for the remainder of the curve.

The term "$AUC_0$-$T_{max}$" is the mean area under the plasma concentration-time curve from time 0 to $T_{max}$ and is used as an indicator of the rate of drug absorption, or metabolite formation. It is calculated as the arithmetic mean of the area under the plasma concentration-time curve from time 0 to $T_{max}$ calculated for each individual participating in the bioavailability study.

The term "$AUC_0$-8" or "$AUC_{inf}$" is the mean area under the plasma concentration-time curve extrapolated to infinity It is calculated as the arithmetic mean of the area under the plasma concentration-time curve from time 0 extrapolated to infinity, calculated for each individual participating in the bioavailability study.

The term "half-life" is the apparent terminal elimination half-life.

The term "HVD" is the half value duration, that is, the time during which clonidine concentrations are above one half the $C_{max}$. This parameter is an indicator of the shape of the plasma concentration time curve.

The term "immediate release" is the release of an active ingredient from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time.

The term "initial administration" is defined for purposes of the present invention as the first single dose of a formulation containing an active ingredient administered to a patient or subject or the first dose administered to a patient or subject after a suitable washout period.

The words "comprise", "comprises", and "comprising" are to be interpreted inclusively rather than exclusively. The works "consist", "consisting", and its variants, are to be interpreted exclusively, rather than inclusively.

As used herein the term "about" means a variability of 10% from the reference given, unless otherwise specified.

A clonidine formulation of the invention has a 24-hour release which provides a single plasma concentration peak, independent of food intake (e.g., could be administered under both fasted and fed conditions). Following a single administration of a formulation containing a coated clonidine-cation exchange resin complex matrix as described herein, the mean peak plasma concentration is reached between about 6 and about 9 hours after dosing; and at least about 70%, or at least about 85% of the 24-hour period for the plasma concentration is above about 200 pg/mL, and the mean maximum peak concentration does not exceed about 580 pg/mL over the 24-hour period. [200 pg/mL has been generally recognized as the minimum effective dose for clonidine use as an antihypertensive agent (see, e.g., US patent application 2008/0152709 "clonidine composition and method of use")].

In another embodiment, a formulation containing the multi-particulate, barrier coated, clonidine-ion exchange resin complex matrix releases clonidine in vivo following a single dose administration such that the duration over which the plasma levels of clonidine is equal or greater than about 50% of the peak plasma concentration is at least about 30 hours. In still another embodiment, a formulation as described herein releases clonidine in vivo following single dose administration such that the duration over which the plasma level of clonidine is equal to or greater than about 75% of the peak plasma concentration is about 6 hours or greater, at least about 12 hours, or at least about 18 hours.

In another embodiment, an oral, once-a-day, modified release clonidine pharmaceutical composition is provided. The composition comprises a pharmaceutically effective amount of a coated complex comprising clonidine bound to a cationic exchange resin which provides a mean plasma concentration in human patients of about 0.4 to about 5.4 ng/mL at about 6.1 to about 9.5 hours following a single clonidine dose of about 0.2 mg. The composition may be either a liquid suspension or a tablet. In one embodiment, the pharmaceutical composition provides a plasma half-life of about 13.7 hours±about 3 hours for clonidine.

Clonidine-Cation Exchange Resin Complexes and Matrixes

Clonidine, N-(2,6-dichlorophenyl)-4,5-dihydro-1H-imidazol-2-amine, is characterized by the structure:

Clonidine hydrocholoride, is an imidazoline derivative and exists as a mesomeric compound. The chemical name is 2-(2,6-dichlorphenylamino)-2-imidazoline hydrochloride. The structural formula is:

In order to prepare a composition of the invention, one or more salts or one or more prodrugs of clonidine, or in a combination of such forms is used for complexation with an ion exchange resin as described herein. Clonidine in the form of its hydrochloride salt is available commercially.

Cationic exchange resins are readily selected for use as described herein. Cationic exchange resins vary in strength, i.e., in their ability to exchange cations. In one embodiment, a relatively strong cationic resin, e.g., Amberlite® IRP69, manufactured by Rohm and Haas; or Duolite® AP143, a chloride form sytrene-divinylbenzene polymeric (cholestyramine resin) is selected. Alternatively, one may select a relatively weak cationic exchange resin, e.g., Amberlite® IRP88 [Rohm and Haas], a weakly acidic potassium form cation exchange resin with 4% cross-linked methacrylate (100 to 500 mesh, equiv to about 150 microns to about 27 microns, ASTM standard) or Amberlite® 64 (a methacrylic acid and divinylbenzene polymer hydrogen form polacrilex resin, Rohm and Haas, purchased with a particle size ranging from 100 to 400 mesh (equiv to 35 microns to 150 microns, ASTM standard size), capacity ~10 meq/g by dry weight). Further, either regularly or irregularly shaped particles may be used as cation exchange resins according to the present invention. Regularly shaped particles are those particles that substantially conform to geometric shapes such as spherical, elliptical, cylindrical and the like, which are exemplified by Dowex® 50WX8 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite® IRP-69 (Rohm and Haas), the use of which is illustrated in the examples below. This cation exchange resin is a sulfonated polymer composed of polystyrene cross-linked with about 8% of divinylbenzene, with an ion-exchange capacity of about 4.5 to 5.5 meq/g of dry resin (H⁺ form). Another cation exchange resin having similar properties is Dowex® 50WX8 (H+ Rhin, linear formula, $C_{10}H_{12}.C_{10}H_{10}.C_9H_8)_x$, 200-400 mesh particle size, which is equivalent to about 75 microns to about 35 microns, ASTM standard). However, Amberlite® IRP-69 consists of irregularly shaped particles with a size range of about 100 to about 500 mesh (about 150 microns to about 27 microns, ASTM standard), whereas the Dowex® 50WX8 is more regularly shaped. Resins are generally purchased with a size ranging from about 25 microns to about 400 microns. However, other sizes may be selected, or larger sized particles may be milled to provide smaller particle sizes.

The selected ion exchange resins may be further treated by the manufacturer or the purchaser to maximize the safety for pharmaceutical use or for improved performance of the compositions. Impurities present in the resins may be removed or neutralized by the use of common chelating agents, antioxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin.

Binding of clonidine to the ion exchange resin can be accomplished using methods known in the art, e.g., in an aqueous slurry. Once formed, the clonidine-ion exchange resin complex is collected by filtration and washed with appropriate solvents to remove any unbound drug or by-products. The complexes can be air-dried in trays, in a fluid bed dryer, or other suitable dryer, at room temperature or at elevated temperature.

The amount of clonidine that can be loaded onto a resin will typically range from about 0.5% to about 50% by weight of the clonidine-ion exchange resin particles, or about 0.75% to about 1% by weight of the clonidine-ion exchange resin particles. A skilled artisan with limited experimentation can determine the optimum loading for any drug resin complex. In one embodiment, loading of about 10% to about 40% by weight, more desirably, about 15% to about 30% by weight, of the drug-ion exchange resin particles can be employed. Typical loadings of about 25% by weight of the drug-ion exchange resin particles can be advantageously employed.

In one embodiment, the composition of the invention contains clonidine complexed to a sodium polystyrene sulfonate resin in at a ratio of about 1 wt clonidine (based on the weight of the clonidine salt) to about 100 wt resin to about 1 wt clonidine (based on the weight of the clonidine salt) to about 300 wt resin. In another embodiment, the clonidine (based on the weight of the salt) to resin ratio is about 1:120 to about 1:180. In yet a further embodiment, the clonidine to resin ratio is about 1:150.

Granulating Agents and Matrix Forming Polymers

As used herein, the term "matrix forming polymer" or "matrix forming polymeric material" refers to a polymer-based solution which forms a matrix with the clonidine-ion exchange resin complex. This term encompasses both those water-insoluble polymers/co-polymers which function as release retardants as described herein, and hydrophilic polymers/co-polymers which have described in the literature as impregnating or solvating agents. Suitably, the matrix forming polymer is non-reactive polymer with clonidine. In one embodiment, an ion exchange resin matrix may include more than one matrix-forming polymer system. For example, a clonidine-ion exchange resin complex matrix may contain both a hydrophilic and a hydrophobic polymer which had been applied, e.g., to facilitate granulation or coating. Such a matrix forming polymer is added in an amount which increases the total weight of the uncoated clonidine-ion exchange resin complex about 3 wt % to about 30 wt %. However, higher or lower amounts may be selected.

In one embodiment, a hydrophilic polymer such as polyvinylpyrrolidone [e.g., such as may be purchased commercially as Kollidon 30] is combined with the clonidine-ion exchange resin complex in order to facilitate granulation prior to coating. Other hydrophilic polymeric granulating agents may include water-soluble polymeric materials which have been described in the art as impregnating agents or solvating agents and which function in the present application as granulating agents. In one embodiment, the granulating agent is a polyethylene glycol. Examples of desirable impregnating/solvating agents include those described in U.S. patent application Ser. No. 11/724,966, filed Mar. 15, 2007, Published as US 2007-0215511A, Sep. 20, 2007, and Meadows, US 2003-0099711, which are incorporated herein by reference, or in U.S. Pat. No. 4,221,778 and published US Patent application Publication No. US 2003/0099711 A1, the disclosures of which are incorporated herein by reference. Specific examples of other impregnating agents include propylene glycol, polyethylene glycol, polyvinyl alcohol, hydroxypropyl methylcellulose, hydroxypropyl cellulose, and sorbitol.

Alternatively, a hydrophobic polymer or a water-insoluble combination of polymers may be selected, such as those which have been described. Such polymers include those which have been previously described as release retardants. As with the other matrix forming polymers, the hydrophobic polymer does not form in a separate layer on the clonidine-ion exchange resin complex, but forms a matrix therewith. Examples of suitable release retardants include, for example, a polyvinyl acetate polymer or a mixture of polymers containing same (e.g., KOLLICOAT SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems. These retardants when used may further prolong or alter the release of the drug from the ion exchange resin complex/matrix and maximize attaining the desired release profile. Further, use of a release retardant permit in some cases lowering the amount of coating thickness needed to attain a prolonged drug release of up to 24 hours. These retardants can be used in either substantially pure form or as a commercial preparation obtained from a vendor. The preferred release retardant is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members polymers including, e.g., members of the EUDRAGIT polymer family, e.g., the L, S, and E, polymers may be selected.

The quantity of a matrix forming polymer typically adds from about 3% to about 30% or more by weight to the total weight of the uncoated clonidine-ion exchange resin complex. In one embodiment, a hydrophobic polymer such as those described as a release retardant is used at the low end of this range, e.g., about 3 to about 10%, or about 5 to about 8%, in order to minimize the release retardant effect. In another embodiment, a hydrophilic polymer is used at the high end of this range, e.g., about 15 to about 30%. In another embodiment, the matrix forming polymer, if used, is in the range from about 5% to about 20% and most preferably in the range of about 10% to about 15% by weight of the uncoated clonidine drug-ion exchange resin complex matrix particles.

These matrix forming polymers can be added after a substantial amount of complex formation has taken place. In the more preferred embodiment, the matrix forming polymer is added after the formation of clonidine-ion exchange resin complex. Upon admixing, the clonidine-ion exchange resin complex particles with the matrix polymer (clonidine-ion exchange resin complex-matrix), the mixture is dried and milled appropriately. In some cases, the milling may be carried out before the complete drying of the clonidine-ion exchange resin complex-matrix and then again further drying followed by milling to obtain the desired characteristics. In one embodiment, the clonidine-ion exchange resin complex matrix is milled or passed through a sieve to provide a particle size ranging from about 40 microns to about 410 microns to enhance mouth feel (i.e., texture), or about 50 microns to about 250 microns. These particles may be either regularly or irregularly shaped. This may be performed both prior to and after application of the matrix forming polymer, if any. In some embodiments, the average particle size of the uncoated clonidine-ion exchange resin complex-optional matrix is milled to a size of about 100 to about 200 microns. These particle sizes maybe determined using sieve analysis through sieve shaking having USP standard wire mesh sieves conforming to ASTM specifications.

Following complexation of clonidine and the ion exchange resin, with optional application of matrix forming polymer, water is typically removed from a wet clonidine-ion exchange resin complex or matrix in order to facilitate application of the barrier coating.

Coating System

Suitably, the composition of the invention contains a barrier coating applied over the clonidine-ion exchange resin complex-optional matrix as an aqueous dispersion, dried, and milled or passed through a screen such that the barrier coated clonidine-ion exchange complex and optional matrix in the size range described herein, i.e., in the range of about 50 to about 410 microns. Suitably, the barrier coat is a non-ionic, water-permeable, water-insoluble pH-independent polymer or blend of polymers which provides a modified release profile to the clonidine.

In one embodiment, the aqueous dispersion is a water insoluble polymer comprising a polyvinyl acetate polymer, or a blend of polymers comprising a polyvinyl acetate polymer. In one embodiment, the barrier coating further contains a plasticizer, which can facilitate uniform coating of the clonidine-ion exchange resin complex-optional matrix and enhances the tensile strength of the barrier coating layer.

One coating composition useful in the present invention is applied in the form of an aqueous dispersion containing an polyvinyl acetate (PVA) polymer based aqueous coating dispersion and a plasticizer. The PVA is insoluble in water at room temperature. The PVA may be used in either substantially pure form or as a blend. Where the barrier coating comprises a PVA polymer, the PVA polymer is present in an amount of about 70% to about 90% w/w of the final barrier coating layer, at least about 75%, at least about 80%, about 85% w/w of the final barrier coating layer. Generally, a plasticizer is used in the percent range, or a mixture of plasticizers combine to total about 2 to about 50% by weight of the coating layer, more preferably about 2.5% to about 20% by weight of the coating layer on the coated clonidine-ion exchange resin complex. Preferably a plasticizer is in a range of about 5% to about 10% by weight of the coating layer based on the coated complex provides the most desirable properties. Suitable plasticizers may be water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor® P (2-pyrrolidone), and mixtures thereof. Other plasticizers are described in patent application publication US 2003/0099711 A1, May 29, 2003, page 4 (0041) the disclosure of which is incorporated herein by reference.

A commercial polyvinylacetate blend contains primarily a polyvinyl acetate polymer, a stabilizer, and minor amounts of a surfactant such as sodium lauryl sulfate. Where the barrier coating comprises PVP as the stabilizer component, the final barrier coating layer generally contains about 5 to about 10% w/w of polyvinyl pyrrolidone. In one desired embodiment, the aqueous based barrier coating solution is KOLLICOAT SR 30 D (BASF Corporation) and whose composition is about 27% PVA polymer, about 2.7% polyvinylpyrrolidone (PVP), about 0.3% sodium lauryl sulfate (solids content 30% w/w), mixed with a plasticizer. See, also, U.S. Pat. No. 6,066,334 and U.S. Pat. No. 6,046,277, which are incorporated by reference herein. The PVP and surfactant help stabilize the aqueous dispersion of the PVA. Generally, such stabilizing components are present in an amount totaling less than about 10% w/w, and preferably less than about 5% w/w. Optionally, a selected surfactant is present in an amount of about 1% or less. In one embodiment, the surfactant is a non-ionic surfactant. Optionally, an ionic surfactant may be selected.

In a particularly desirable embodiment, the desired modified release is obtained when the coating layer formed by application of the aqueous dispersion containing the KOLLICOAT™ SR-30D-plasticizer is dried and cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C. Thus, in one embodiment, the clonidine-ion exchange resin complex-optional matrix has a cured water-permeable, high tensile strength, water insoluble, barrier coating comprising a non-ionic polymer and a plasticizer and having an elongation factor in the range of about 150% to 400%. In one embodiment, the barrier coating comprises a polyvinyl acetate polymer, a stabilizer, a surfactant and a plasticizer. In one embodiment, a barrier coating comprises about 2.5 to about 10% of plasticizer, about 70 to about 90% polyvinylacetate, about 5 to about 10% polyvinylpyrrolidone, and about 0.1 to about 1% surfactant.

Optionally, another barrier coating may be selected. See, e.g., the barrier coatings described in Kolter et al, U.S. Pat. No. 6,066,334 and U.S. Pat. No. 6,046,277 and Mehta et al, US Published Patent Application No. US 2007-0215511A, published Sep. 20, 2007, and its counterpart application, WO 2007/109104, which are incorporated herein by reference. See, also, e.g., Wen, U.S. Pat. Nos. 6,046,277 and 6,001,392; Meadows, US Published Patent Application No. 2003/009971 and related application WO 03/020242; Sovereign Pharmaceuticals, WO 2006/022996 and related applications US Published Patent Application Nos. US2005/232986; US2005/232987; US2005/232993; US2005/266032.

Alternatively, other known aqueous or non-aqueous barrier coatings have been described in the literature and/or which are commercially available could be used for the coating process, but are less desirable for the reasons described in US Patent Publication No. US 2007-0215511A and in the literature cited in the background therein. See, e.g., Bess, et al, U.S. Pat. No. 7,067,116; Goede et al, U.S. Pat. No. 6,667,058, Wen et al, U.S. Pat. No. 6,001,392, among others. Such coating materials include ethylcellulose based extended release coatings, e.g., Aquacoat™ ethylcellulose polymer extended release coating and Surelease®. Surelease® is available from Colorcon as an aqueous ethyl cellulose dispersion containing water (70.6% w/w), ethylcellulose (18.8% w/w), ammonium hydroxide (4.4% w/w), a medium chain triglyceride (4.0% w/w), and oleic acid (2.2% w/w).

In one embodiment, the barrier coating layer is about 10% to about 70%, by weight, of the uncoated clonidine-ion exchange resin complex-optional matrix. In another embodiment, the barrier coating layer is about 30% to about 50% by weight of the uncoated clonidine-ion exchange resin complex-optional matrix, about 40% by weight of the clonidine-ion exchange resin complex-optional matrix prior to coating.

In another embodiment, the coating may be a EUDRAGIT™ brand acrylate based coating materials [including, e.g., a poly(ethyl acrylate-co-methyl methacrylate-co-trimethylammonioethyl methacrylate chloride) polymer system]. For example, Eudragit Eudragit™ RS 30D [a pH-independent, 30% aqueous dispersion of poly(ethyl acrylate-co-methyl methacrylate-co-trimethylammonioethyl methacrylate chloride) 1:2:0.1)], or Eudragit™ RL 30D [a 30% aqueous dispersion, pH independent polymer, poly(ethyl acrylate-co-methyl methacrylate-co-trimethylammonioethyl methacrylate chloride) 1:2:0.2)] may be selected as the barrier coating. Typically, talc is added to these coatings to address issues associated with tackiness during processing and these coatings are not cured.

Following coating, the coating is dried and is cured. The coating is typically cured for about 1 to about 24 hours. In alternate embodiments, the coating is cured for about 4 to about 16 hours, and preferably about 5 hours at high temperature, e.g., about 50° C. to about 65° C., and preferably about 60° C.

The formulations of the invention are designed to provide a once-a-day administrable, 24-hour effective dose, having a single peak in its release profile. In one embodiment, a composition of the invention has the fasting pK profile of the test compound in FIG. 1. In still another embodiment, a composition has the fed pK profile of the test compound in FIG. 1. In other embodiments, a composition of the invention has a fasting pK profile of the test compound in FIG. 2. In still other embodiments, a composition of the invention has a fed pK profile of the test compound in FIG. 2. In one embodiment, the present invention provides a oral single dosage unit, which provides an in vitro dissolution profile of about 30% at one hour; about 25% to about 55% at 3 hours; about 40% to about 75% at 6 hours; and not less than 70% at 24 hours, and having a therapeutically effective plasma concentration for at least about 70%, and preferably at least about of the twenty-four hour period following the single oral dose.

In one embodiment, the invention provides an oral clonidine pharmaceutical composition comprising a once-a-day modified release formulation, which is not affected by food. The extended release clonidine composition comprises a pharmaceutically effective amount of a coated complex comprising clonidine bound to a cationic exchange resin (optionally in a matrix) which provides a mean plasma concentration in human patients of about 0.5 ng/mL at about 6 to about 10 hours following a single clonidine dose of about 0.2 mg. The composition may be in the form of a liquid suspension or a tablet. In one embodiment, the plasma half-life of clonidine following a single dose of the composition of the invention is about 10 to about 18 hours. In another embodiment, the extended release clonidine composition comprises a pharmaceutically effective amount of a coated complex comprising clonidine bound to a cationic exchange resin (optionally in a matrix) which provides a mean plasma concentration in human patients of about 0.49 (±0.09) ng/mL at 7.8 hours (±1.7 hours) following a single clonidine dose of about 0.2 mg. The composition may be in the form of a liquid suspension or a tablet. In one embodiment, the plasma half-life of clonidine following a single dose of the composition of the invention is 13.7 hours±3 hours.

Finished Dose Formulations

The clonidine-ion exchange resin complex-optional matrix of the present invention, can readily be formulated with pharmaceutically acceptable excipients according to methods well known to those of skill in the art. In one embodiment, these formulations contain a substantially barrier coated clonidine-ion exchange resin complex of the invention, optionally with a matrix.

The clonidine-ion exchange resin complex-optional matrix composition thus prepared may be stored for future use or promptly formulated with conventional pharmaceutically acceptable carriers to prepare finished ingestible compositions for delivery orally, nasogastric tube, or via other means. The compositions according to this invention may, for example, take the form of liquid preparations such as suspensions, or solid preparations such as capsules, tablets, caplets, sublinguals, powders, wafers, strips, gels, including liquid-gels, etc. In one embodiment, a tablet of the invention is formulated as an orally disintegrating or chewable tablet. Such orally dissolving tablets may disintegrate in the mouth in less than about 60 seconds.

Additionally, the barrier coated clonidine-ion exchange resin complex-optional matrix compositions may be formulated using conventional pharmaceutically acceptable carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

Suitable thickeners include, e.g., tragacanth; xanthan gum; bentonite; starch; acacia and lower alkyl ethers of cellulose (including the hydroxy and carboxy derivatives of the cellulose ethers). Examples of cellulose include, e.g., hydroxypropyl cellulose, hydroxypropyl methyl cellulose, sodium carboxy methylcellulose, microcrystalline cellulose (MCC), and MCC with sodium carboxylmethyl cellulose. In one embodiment, tragacanth is used and incorporated in an amount of from about 0.1 to about 1.0% weight per volume (w/v) of the composition, and more preferably about 0.5% w/v of the composition. Xanthan gum is used in the amount of from about 0.025 to about 0.5% w/v and preferably about 0.25% w/v. The compositions may include a humectant composition to give the liquid greater viscosity and stability. Suitable humectants useful in the finished formulations include glycerin, polyethylene glycol, propylene glycol and mixtures thereof.

The oral liquid compositions of the present invention may also comprise one or more surfactants in amounts of up to about 5.0% w/v and preferably from about 0.02 to about 3.0% w/v of the total formulation. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20) sorbitan monooleate and sorbitan monooleate. These are commercially known as TWEENS and SPANS and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added functions to keep any flavors and sweeteners homogeneously dissolved and dispersed in solution.

Suitable polysorbates include polysorbate 20, polysorbate 40, polysorbate 80 and mixtures thereof. Most preferably, polysorbate 80 is employed. The surfactant component will comprise from about 0.01 to about 2.0% w/v of the total composition and preferably will comprise about 0.1% w/v of the total weight of the composition.

A second emulsifer/surfactant useful in combination with polysorbates may be employed and is preferably a poloxamer such as Poloxamer 407. Poloxamer 407 has an HLB (hydrophilic/lipophilic balance) of about 22 and is sold under the tradename Pluoronic-127 (BASF-NJ). The two surfactants can be employed in substantially equivalent amounts. For example, the Poloxamer 407 and polysorbate 80 may each be employed together at levels of approximately from about 0.02 to about 4.0% w/v of the total weight of the formulation.

Aqueous suspensions may be obtained by dispersing the clonidine-ion exchange resin compositions in a suitable aqueous vehicle, optionally with the addition of suitable viscosity enhancing agent(s) (e.g., cellulose derivatives, xanthan gum, etc). Non-aqueous suspensions may be obtained by dispersing the foregoing compositions in a suitable non-aqueous based vehicle, optionally with the addition of suitable viscosity enhancing agent(s) (e.g., hydrogenated edible fats, aluminum state, etc.). Suitable non-aqueous vehicles include, for example, almond oil, arachis oil, soybean oil or soybean oil or fractionated vegetable oils such as fractionated coconut oil.

Useful preservatives include, but are not limited to, sodium benzoate, benzoic acid, potassium sorbate, salts of edetate (also known as salts of ethylenediaminetetraacetic acid, or EDTA, such as disodium EDTA), parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetraacetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis[ethyliminodi(acetic acid)] (EGTA); 1,10-bis(2-pyridylmethyl)-1,4,7,10-tetraazadecane (BPTETA); ethylenediamine (EDAMINE); Trans-1,2-diaminocyclohexane-N,N,N',N'-tetraacetic acid (CDTA); ethylenediamine-N, N'-diacetate (EDDA); phenazine methosulphate (PMS); 2,6-Dichloro-indophenol (DCPIP); Bis(carboxymethyl)diaza-18-crown-6 (CROWN); porphine; chlorophyll; dimercaprol (2,3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative. Methods for evaluating the efficacy of preservatives in pharmaceutical formulations are known to those skilled in the art. Preferred preservatives are the paraben preservatives include, methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 16:1, preferably 9:1.

In the instance where auxiliary sweeteners are utilized, the present invention contemplates the inclusion of those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, high fructose corn syrup, dextrose, sucrose, sugar, maltose, partially hydrolyzed starch, or corn syrup solids and sugar alcohols such as sorbitol, xylitol, mannitol and mixtures thereof;

In general, the amount of sweetener will vary with the desired amount of sweeteners selected for a particular liquid formulation. This amount will normally be 0.001 to about 90% by weight, per volume of the final liquid composition, when using an easily extractable sweetener. The water-soluble sweeteners described above, are preferably used in amounts of about 5 to about 70% by weight per volume, and most preferably from about 10 to about 50% by weight per volume of the final liquid composition. In contrast, the artificial sweeteners [e.g., sucralose, acesulfame K, and dipeptide based sweeteners] are used in amounts of about 0.005 to about 5.0% and most preferably about 0.01 to about 2.5% by weight per volume of the final liquid composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e. thymol, eculyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

The colorants useful in the present invention, include the pigments such as titanium dioxide, that may be incorporated in amounts of up to about 1% by weight per volume, and preferably up to about 0.6% by weight per volume. Also, the colorants may include dyes suitable for food, drug and cosmetic applications, and known as D&C and F.D. & C. dyes and the like. The materials acceptable for the foregoing spectrum of use are preferably water-soluble. Illustrative examples include indigoid dye, known as F.D. & C. Blue No. 2, which is the disodium salt of 5,5' indigotindisulfonic acid. Similarly, the dye known as F.D. & C. Green No. 1 comprises a triphenylmethane dye and is the monosodium salt of 4-[4-N-ethyl p-sulfobenzylamino)diphenylmethylene]-[1-(N-ethyl-N-p-sulfoniumbenzyl)-2,5-cyclohexadienimine] A full recitation of all F.D. & C. and D. & C. and their corresponding chemical structures may be found in the Kirk-Othmer Encyclopedia of Chemical Technology, in Volume 5, at Pages 857-884, which text is accordingly incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a suspension, to flocculate. Those skilled in the art are well versed in suitable empirical methods to determine the appropriate wetting agents and concentrations to achieve optimum dispersion and avoid flocculation. Suitable wetting agents are listed in the US Pharmacopeia 32.

In another aspect, the invention provides a product containing a coated clonidine-ion exchange resin complex-optional matrix of the invention. In some embodiments, the coated clonidine-ion exchange resin complex-optional matrix of the invention are in packs in a form ready for administration, e.g., a blister pack, a bottle, syringes, foil packs, pouches, or other suitable container. In other embodiments, the compositions of the invention are in concentrated form in packs, optionally with the diluent required to make a final solution for administration. In still other embodiments, the product contains a compound useful in the invention in solid form and, optionally, a separate container with a suitable suspension base or other carrier for the drug-ion exchange resin complex useful in the invention. In still other embodiments, the above packs/kits include other components, e.g., a meter dose apparatus/device, instructions for dilution, mixing and/or administration of the product, other containers, nasogastric tubes, etc. Other such pack/kit components will be readily apparent to one of ordinary skill in the art.

Methods and apparatus for delivery of drugs through nasogastric tubes are well known to those of ordinary skill in the art. See, e.g., E. Bryson, "Drug Administration via Nasogastric Tube", *Nurs Times,* 2001, Apr. 19-25 97(16):51. The present invention can be readily delivered using such devices. Suitable nasogastric tubes are available commercially and/or have been described. See, e.g., U.S. Pat. No. 5,334,166; U.S. Pat. No. 5,322,073; U.S. Pat. No. 4,619,673; U.S. Pat. No. 4,363,323.

Uses of Formulations

The formulations described herein are useful for delivering a twenty-four hour extended release profile of clonidine in a single oral dose. Suitably, the method involves administering to a subject a single oral clonidine dosage unit as described herein. In one embodiment, the single oral clonidine dose is administered at night-time. The formulations of the invention provide a therapeutically effective amount of clonidine for a twenty-four hour release profile which provides a single peak plasma concentration, following a single administration of the oral clonidine dose.

Clonidine has been found useful in treatment of a wide range of diseases and disorders, not all of which are known to be mediated by catecholamines or even related to a-adrenergic activity. A list of therapeutic uses of clonidine has been compiled, for example, by Fagan et al. (2006) U.S. Pharmacist 5:HS2-HS16, which is incorporated by reference herein without admission that it constitutes prior art to the present invention. This and other publications describe diseases or disorders for which clonidine is indicated as including, e.g., circulatory disorders including hypertension and cardiovascular disease related thereto, arrhythmia, myocardial ischemia, atrial fibrillation, congestive heart failure, allodynia, hyperalgesia, neuropathic pain, cancer pain, cluster headache, chronic headache, migraine, postoperative pain, spinal cord injury pain, akathisia, restless legs syndrome, peripheral neuropathy, neuralgia, orofacial pain, diabetic gastroparesis, chronic memory disorders, hypertonia, hyperkinetic movement disorders, Tourette's syndrome, substance withdrawal, attention deficit hyperactivity disorder, manic states, behavioral disorders related to encephalopathy, bipolar disorder, narcolepsy, post-traumatic stress disorder, schizophrenia, sleep disorders, social phobia, hyperthyroidism, growth delay, excessive sweating, hot flashes, trichorrhexis nodosa, and combinations thereof. Clonidine has also been described as being useful to treat pain and/or inflammation in, e.g., US Published Patent Application No. 2009/026449 A1 (Oct. 22, 2009), which describes conditions including, e.g., pain due to a spinal disc herniation (i.e., sciatica), spondilothesis, stenosis, osteoarthritis, carpal/tarsal tunnel syndrome, tendonitis, temporomandibular joint disorder (TMJ) and discogenic back pain and joint pain, as well as pain that accompanies or follows surgery.

Optionally, a modified release formulation may contain one or more immediate release components. For example, the modified release, coated clonidine-cation exchange resin-optional matrix particles described herein may be formulated with an active component which may be in immediate release form. By "immediate release", it is meant for purposes of the present invention that the formulation containing the therapeutically active agent(s) meets the disintegration and/or dissolution requirements for immediate release of the particular therapeutically active agent(s), as set forth in the USP XXII, 1990 (The United States Pharmacopeia). Generally, immediate release formulations involve release of more than about 50% of the active agent in less than about 1 hour and greater than about 70% of the active agent in about 6 hours.

Several formulations prepared according to the present invention have been prepared and release profiles assessed using a variant of the USP Standard Paddle tester. Twenty-four release profiles have been observed for all of the formulations prepared by the working examples described below.

The following examples illustrate the compositions of the inventions. These formulations are not limitations on the present invention.

EXAMPLES

Example 1

Preparation of Clonidine Tablet Formulation: Barrier Coated Clonidine-Cation Exchange Resin Complex Matrix Modified Release Tablets, Equivalent to 0.2 mg Clonidine HCl:

A. Preparation of Uncoated Clonidine-Cation Exchange Resin Complex Matrix

| Ingredients | Grams/batch |
| --- | --- |
| Clonidine HCl | 85 |
| Sodium Polystyrene Sulfonate (Amberlite ™ IRP-69) Cation Exchange Resin | 12750 |
| Povidone (Kollidon ® 30) | 1134 |
| Purified Water* | qs* |

*Removed during processing

The clonidine-resin complex matrix was prepared by first adding 80 L of purified water into a vessel and dissolving clonidine HCl therein by continuous mixing. A sodium polystyrene sulfonate ion exchange resin (AMBERLITE™ IRP-69) was dispersed with continuous mixing to form a slurry and the mixing was continued for 60 minutes to permit formation of a clonidine-ion exchange resin complex. Water from the slurry was removed by filtration. The wet resin complex was rinsed twice using purified water and then dried until the moisture content was about 10% to about 20%. In a separate container, povidone (Kollidon® 30) was dissolved into 2.834 kg of purified water (povidone solution). The povidone solution was then sprayed onto the wet resin complex with continuous mixing to form a uniform clonidine-resin complex matrix. The resulting matrix granules were dried until the moisture content was in the range of 10 to 20%. These semi-dried granules (clonidine-ion exchange resin complex matrix) were then milled using CO-MIL® brand mill fitted with a 40 mesh screen. The granules were further dried to a moisture content of in the range of about 3% to about 7%. These dried granules were passed through a 40 mesh screen using the CO-MIL® brand mill.

B. Coated Clonidine Cation Exchange Resin Complex Matrix

| Ingredients | gms |
|---|---|
| Uncoated Clonidine-Cation Exchange Resin Matrix of Part A | 3200 |
| Polyvinyl Acetate dispersion (Kollicoat ® SR 30D)** | 4063** |
| Triacetin USP | 61 |
| Purified Water* | 2276 |

*Removed during processing, **contains 30% w/w solids

The coated clonidine-ion exchange resin complex matrix was prepared as follows. The coating solution was prepared by mixing triacetin, purified water and polyvinyl acetate dispersion (purchased commercially as KOLLICOAT® SR-30D, from BASF) in a container. The coating solution was passed though a [ASTM standard] Sieve No. 40 mesh screen. The coating process was performed in a VECTOR FLM-5™ fluid bed processor equipped with a Wurster column by applying 6.4 kg of coating solution to 3.2 kg of the uncoated clonidine-cation exchange resin matrix prepared as in Part A, to afford the matrix with a 40% weight gain. The coated clonidine-cation exchange resin complex matrix was then passed through an ASTM standard sieve No. 40 mesh screen and placed in a hot air oven at 60° C. for 5 hours. The cured, barrier coated complex matrix was again passed through No. 40 mesh screen (i.e., about 410 microns).

C. Clonidine 24-hour Release Tablet, 0.2 mg Formula

| Ingredient | mg/Tablet | kg/125,000 tablets |
|---|---|---|
| I. Core Tablet | | |
| Coated Clonidine-Cation Exchange Resin Complex Matrix of Part B | 49.61 | 6.201 |
| Lactose Monohydrate | 50.00 | 6.250 |
| Microcrystalline Cellulose | 188.39 | 23.549 |
| Crospovidone | 9.00 | 1.125 |
| Dental-Type silica | 1.50 | 0.1875 |
| Magnesium Stearate | 1.50 | 0.1875 |
| Total | 300.00 | 37.500 |
| II. Coated Tablet | | |
| Opadry White YS-1-18202-A | 9.00 | 1.125 |
| Purified Water** | Qs | Qs |
| Total | 309.00 | 38.625 |

*Actual quantity may vary based on assay value, **Removed during processing

Lactose monohydrate, crospovidone, coated Clonidine-cation exchange resin matrix of Part B, dental-type silica, and microcrystalline cellulose were screened through #40 mesh screen and mixed using 'V'Blender for 10 minutes. Magnesium stearate was screened through #40 mesh screen and added in a 'V'Blender [5 cubic ft size, Patterson Kelly. Mixing continues for 5 minutes. The powder blend from 'V' blender was compressed into tablets (equivalent to 0.2 mg clonidine HCl) at 3 to 10 kp hardness using 0.5200"X0.2385" capsule shape toolings (core tablets). A top coating solution was prepared by dispersing Opadry White YS-1-18202-A in purified water. Coating process was performed in perforated coating pan by spraying coating solution on core tablets. In an in vitro dissolution profile, the amount of clonidine released from the above-referenced dosage was observed to be not more than 30% at 1 hour; about 25% to about 55% at 3 hours; about 40% to about 75% at 6 hours; and not less than 70% at 24 hours.

Example 2

Barrier Coated Clonidine-Cation Exchange Resin Complex Matrix Tablets, Equivalent to 0.3 mg Clonidine HCl:

A. Preparation of Uncoated Clonidine-Cation Exchange Resin Complex Matrix

| Ingredients | gms/Batch |
|---|---|
| Clonidine HCl | 85 |
| Sodium Polystyrene Sulfonate (Amberlite ™ IRP-69) Cation Exchange Resin | 12750 |
| Povidone (Kollidon ® 30) | 1134 |
| Purified Water* | Qs* |

*Removed during processing

The clonidine-cation exchange resin complex was prepared by adding 80 L of purified water in to a vessel and then clonidine HCl, which was dissolved by continuous mixing. Sodium polystyrene sulfonate (AMBERLITE™ IRP-69) was dispersed in the vessel with continuous mixing to form a slurry and the mixing was continued for 60 minutes in order to permit formation of the clonidine-cation exchange resin complex. Water from the slurry was removed by filtration process. The wet clonidine-ion exchange resin complex was rinsed twice using purified water. This wet resin complex was then dried until the moisture content was about 10-20%. In a separate container povidone (Kollidon™ 30) was dissolved in to 2.834 kg of purified water (povidone solution). The povidone solution was then sprayed on to the wet clonidine-cation exchange resin complex with continuous mixing to form a uniform matrix. The resulting clonidine-ion exchange resin complex matrix granules were dried until the moisture content was between 10-20%. The semi-dried granules were then milled using CO-MIL™ brand mill fitted with a 40 mesh screen. The granules were further dried to a moisture content of around 3-7%. These dried clonidine-ion exchange resin complex matrix granules were again passed through a CO-MILT™ fitted with a 40 mesh screen.

B. Coated Clonidine-Cation Exchange Resin Complex Matrix

| Ingredients | gms/Batch |
|---|---|
| Clonidine-Cation Exchange Resin Matrix (as prepared in Part A) | 3200 |

-continued

| Ingredients | gms/Batch |
|---|---|
| Polyvinyl Acetate dispersion (Kollicoat SR 30D)** | 4063** |
| Triacetin USP | 61 |
| Purified Water* | 2276 |

*Removed during processing, **contains 30% w/w solids

The coated clonidine-cation exchange resin complex matrix was prepared as follows. The coating solution was prepared by mixing triacetin, purified water and polyvinyl acetate dispersion (purchased from BASF as KOLLICOAT™ SR-30D) in a container. The coating solution was passed though a Seive No. 40 mesh screen. The coating process was performed in a VECTOR FLM-5™ Fluid bed processor equipped with a wurster column by applying 6.4 kg of coating solution to 3.2 kg of clonidine-cation exchange resin complex matrix prepared as described in Part A of this example, to provide a 40% weight gain. The coated clonidine-cation exchange resin complex matrix was then passed through a No. 40 mesh screen and placed in a hot air oven at 60° C. for 5 hours. The cured, barrier coated clonidine-cation exchange resin complex matrix was again passed through No. 40 mesh screen.

C. Clonidine 24-hour Tablet, 0.3 mg Formula

| Ingredient | mg/Tablet | Kg/125,000 tablets |
|---|---|---|
| I. Core Tablet | | |
| Coated Clonidine-Cation exchange resin complex matrix (prepared as described in part B) | 74.42 | 9.302 |
| Lactose Monohydrate | 75.00 | 9.375 |
| Microcrystalline Cellulose | 282.58 | 35.323 |
| Crospovidone | 13.50 | 1.688 |
| Dental-Type silica | 2.25 | 0.281 |
| Magnesium Stearate | 2.25 | 0.281 |
| Total | 450.00 | 56.250 |
| II. Coated Tablet | | |
| Opadry II Yellow 57U92682 | 13.50 | 1.688 |
| Purified Water** | Qs | Qs |
| Total | 463.50 | 57.938 |

*Actual quantity may vary based on assay value, **Removed during processing

Lactose monohydrate, crospovidone, the coated clonidine-cation exchange resin complex matrix prepared as described in part B of this example, dental-type silica and microcrystalline cellulose were screened through #40 mesh screen and mixed using 'V' Blender [5 cubic ft size, Patterson Kelly] for 10 minutes. Magnesium stearate was screened through #40 mesh screen and added in to 'V'Blender, where mixing was continued for 5 minutes. The powder blend from the 'V' blender was compressed into tablets (equivalent to 0.3 mg clonidine HCl) at 4 to 12 kp hardness using 0.5950"X0.2730" capsule shape toolings (core tablets). A top coating solution was prepared by dispersing Opadry II yellow 57U92682 in purified water. The coating process was performed in perforated coating pan by spraying coating solution on core tablets.

Example 3

Preparation of Barrier Coated Clonidine-Ion Exchange Resin Complex Matrix Liquid Suspension Formulation A. Preparation of Uncoated Clonidine-Cation Exchange Resin Complex Matrix

| Ingredients | gms/Batch |
|---|---|
| Clonidine HCl | 85 |
| Sodium Polystyrene Sulfonate (Amberlite ™ IRP-69) Cation Exchange Resin | 12750 |
| Povidone (Kollidon ™ 30) | 1134 |
| Purified Water* | Qs* |

*Removed during processing

The clonidine-cation exchange resin complex was prepared by first adding into a vessel 80 L of Purified Water and dissolving clonidine HCl therein by continuous mixing. A sodium polystyrene sulfonate cation exchange resin (AMBERLITE™ IRP-69) was dispersed with continuous mixing to form a slurry and the mixing was continued for 60 minutes in order to permit complexation of the clonidine and the cation exchange resin. Water from slurry was removed by filtration process. The wet clonidine-cation exchange resin complex was rinsed twice using purified water. This wet resin complex was then dried until the moisture content was in the range of about 10 to about 20%. In a separate container Povidone (Kollidon™ 30) was dissolved in 2.834 kg of Purified Water (Povidone solution). The Povidone solution was then sprayed on to the wet resin complex with continuous mixing to form a uniform matrix. The resulting clonidine-ion exchange resin complex matrix granules were dried until the moisture content was in the range of about 10 to about 20%. The semi-dried granules were then milled using CO-MIL™ fitted with 40 mesh screen. The granules were further dried to a moisture content of around 3-7%. These dried clonidine-ion exchange resin complex matrix granules were again passed through a CO-MILT™ mill fitted with a 40 mesh screen.

B. Coated Clonidine-Cation Exchange Resin Complex Matrix

| Ingredients | gms/Batch |
|---|---|
| Uncoated Clonidine-Cation Exchange Resin Complex Matrix (Prepared as in Part A) | 3200 |
| Polyvinyl Acetate dispersion (Kollicoat SR 30D)** | 4063** |
| Triacetin USP | 61 |
| Purified Water* | 2276 |

*Removed during processing, **contains 30% w/w solids

The coated clonidine-cation exchange resin matrix was prepared as follows. The coating solution was prepared by mixing triacetin, purified water and polyvinyl acetate dispersion (purchased from BASF as KOLLICOAT™ SR-30D) in a separate container. The coating solution was passed though a Seive No. 40 mesh screen. The coating process was performed in a VECTOR FLM-5™ Fluid bed processor equipped with a Wurster column by applying 6.4 kg of coating solution to 3.2 kg of the uncoated clonidine-cation exchange resin complex matrix, that resulted in 40% weight gain. The coated clonidine-cation exchange resin complex matrix was then passed through a Seive No. 40 mesh screen and placed in a hot air oven at 60° C. for 5 hours. The cured, barrier coated clonidine-cation exchange resin complex matrix was passed through a 40 mesh screen.

C. Preparation of Clonidine 24-Hour Release Suspension (Equivalent to 0.1 Mg Clonidine HCl Per mL)

| Ingredient | Kg/Batch |
|---|---|
| Purified Water | 85.2 |
| Citric Acid | 0.379 |
| Polysorbate 80K | 0.208 |
| High Fructose Corn Syrup 42 | 56.8 |
| Sucrose | 28.4 |
| Starch Instant Clearjel (anhydrous) | 4.35 |
| Glycerin | 18.93 |
| Propylparaben | 0.038 |
| Methylparaben | 0.34 |
| Xanthan Gum (anhydrous) | 0.38 |
| Coated Clonidine-Cation Exchange Resin Matrix of Part B | 4.69 |
| Strawberry Banana flavor | 2.124 |
| Purified Water | Qs to 189.3 L |

In order to prepare the coated clonidine-cation exchange resin matrix liquid suspension formulation, 85.2 kg of purified water was added into a main process vessel. Citric acid, polysorbate 80, high fructose corn syrup and sucrose were added and mixed until dissolved. Instant Clearjel was slowly dispersed using high shear mixer. Glycerin was weighed in a separate container and heated to 60-70° C. Propylparaben and methylparaben were added into the heated glycerin (60-70° C.) and mixed until completely dissolved (Paraben Solution). Paraben Solution was cooled down to room temperature and xanthan gum was added (Gum dispersion). Gum dispersion was added into the main process vessel, while mixing with a high shear mixer. The coated clonidine-cation exchange resin matrix prepared according to part B of this Example was added slowly followed by strawberry Banana flavor was added. The final suspension was obtained by adjusting the volume to 189.3 L using Purified water.

Example 4

In Vivo Plasma Profile

Figure 1:
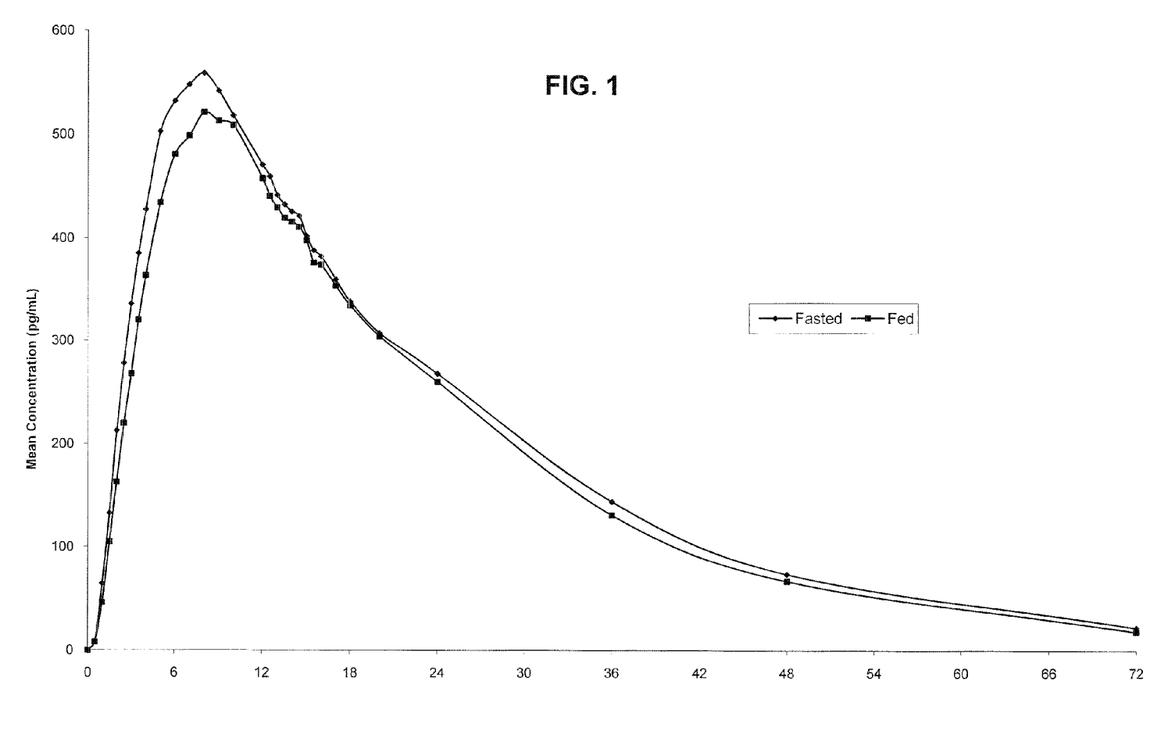
FIG. 1 provides a graph illustrating the mean clonidine concentration-time profiles after administration of a clonidine formulation of the invention in tablet form under fasting condition () and profile of a clonidine formulation of the invention in tablet form (open triangle ▲) under fed condition or presence of food. A single dose of the test tablet formulation which contains 0.2 mg (clonidine HCl equivalent, 0.17 clonidine free base) was administered. A single peak is obtained for the test tablet formulation of the invention, independent of presence of food. The blood plasma profile of the test tablet formulation of the invention demonstrates that the formulation of the invention provides twenty-four hour blood plasma levels.

A. Bioavailability Study of Coated Clonidine-Cation Exchange Resin Matrix Tablets An open-label, randomized, three-period, three-treatment crossover, 26-healthy adult subject study was conducted for the pharmacokinetic study. Subjects received separate single-dose administration under fasted and fed conditions of 0.2 mg coated clonidine-cation exchange resin matrix tablet prepared as described in Example 1. Subjects also received Catapres IRO (1×0.1 mg) administered at 0 and 12 hours after fasted condition. Blood samples were collected prior to and following each dose at selected times through 72 hours post-dose. The plasma samples were analyzed for Clonidine using a validated LC-MS-MS method. The mean concentration-time profile is shown in FIG. 1.

For the 0.2 mg dose from a single oral dose of the tablet of Example 2 under both fasted and fed conditions, the mean peak plasma concentration under both fasted and fed conditions is reached between 6-9 hours after dosing; the mean 24-hour plasma concentration is above the 12-hour concentration of the reference IR formulation (dosed twice at 0 and 12 hour) under the same test condition; at least 85% of the 24-hour period is above the trough concentration of the immediate release product (dosed twice at 0 and 12 hour) at 12 hour; at least 85% of the 24-hour period for the plasma concentration is above 200 pg/mL; the mean maximum peak concentration does not exceed 580 pg/mL over the 24-hour period.

| | Cmax (pg/mL) | $AUC_{last}$ (hr * pg/mL) | $AUC_{inf}$ (hr * pg/mL) | Number of subjects |
|---|---|---|---|---|
| Clonidine Tablets, 0.2 mg (Fasted condition) | 575 ± 108 | 14090 ± 3186 | 14560 ± 3352 | 25 |
| Clonidine Tablets, 0.2 mg (Fed condition) | 539 ± 105 | 13160 ± 3258 | 13560 ± 3389 | 26 |

Figure 2:
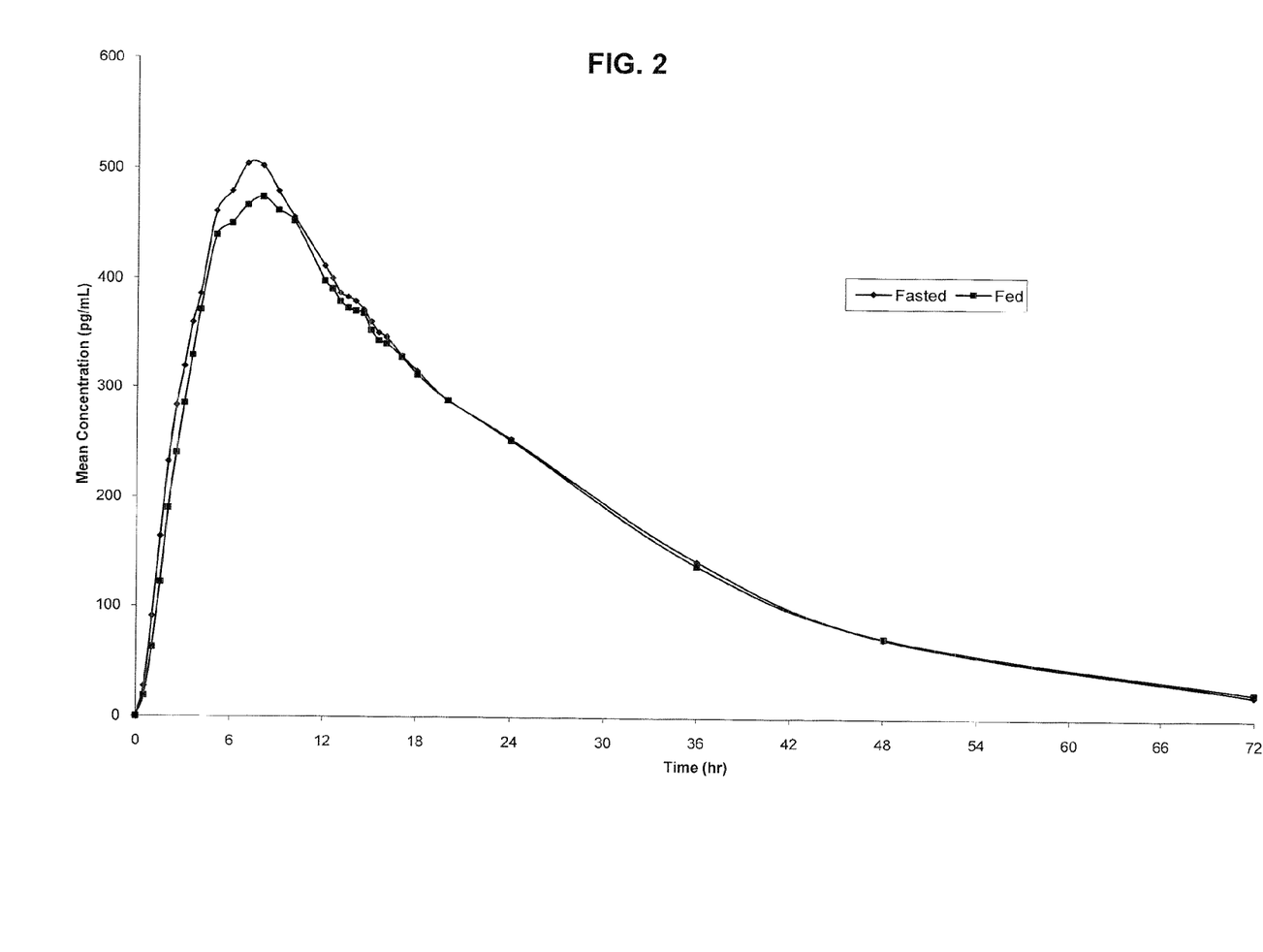
FIG. 2 provides a graph illustrating the mean clonidine concentration-time profiles after administration of a clonidine liquid suspension formulation of the invention under fasting condition () and the profile of a clonidine liquid suspension formulation of the invention (open triangle ▲) under fed condition or presence of food. A single dose of the test liquid suspension formulation which contains 0.2 mg clonidine (clonidine HCl equivalent, 0.17 clonidine free base) was administered. A single peak is obtained for the test liquid suspension formulation of the invention, independent of presence of food. The blood plasma profile of the test suspension formulation of the invention demonstrates that the formulation of the invention provides twenty-four hour blood plasma levels.

B. Bioavailability Study of Coated Clonidine-Cation Exchange Resin Matrix Oral Suspension An open-label, randomized, three-period, three-treatment crossover, 26-healthy adult subject study was conducted for the pharmacokinetic study. Subjects received under either fasted or fed conditions separate single-dose administration of the oral suspension containing the coated clonidine-cation exchange resin matrix prepared as described in Example 3, with the exception that that amount of the coated clonidine-cation exchange resin in Example 3C was doubled (to 9.38 kg/batch) in order to prepare a 0.2 mg/mL dosage form. Subjects also received Catapres IRO (1×0.1 mg) administered at 0 and 12 hours after fasted condition. Blood samples were collected prior to and following each dose at selected times through 72 hours post-dose. The plasma samples were analyzed for Clonidine using a validated LC-MS-MS method. The mean concentration-time profile is shown in FIG. 2.

For the 0.2 mg dose from a single oral dose of the liquid suspension prepared as described above, under both fasted and fed conditions, the mean peak plasma concentration under both fasted and fed conditions is reached in the range of 6 to 9 hours after dosing; the mean 24-hour plasma concentration is above the 12-hour concentration of the reference IR formulation (dosed twice at 0 and 12 hour) under the same test condition; at least 85% of the 24-hour period is above the trough concentration of the immediate release product (dosed twice at 0 and 12 hour) at 12 hour; at least 85% of the 24-hour period for the plasma concentration is above 200 pg/mL; the mean maximum peak concentration does not exceed 580 pg/mL over the 24-hour period.

| | Cmax (pg/mL) | $AUC_{last}$ (hr * pg/mL) | $AUC_{inf}$ (hr * pg/mL) | Number of subjects |
|---|---|---|---|---|
| Clonidine suspension, 0.2 mg (Fasted condition) | 516 ± 85.3 | 13040 ± 2378 | 13640 ± 2627 | 24 |

-continued

| | Cmax (pg/mL) | AUC$_{last}$ (hr * pg/mL) | AUC$_{inf}$ (hr * pg/mL) | Number of subjects |
|---|---|---|---|---|
| Clonidine suspension, 0.2 mg (Fed condition) | 488 ± 89.4 | 12830 ± 3035 | 13370 ± 3393 | 25 |

Example 5

Preparation of Ethylcellulose-Coated Clonidine-Cation Exchange Resin Matrix

A. Clonidine-Cation Exchange Resin Matrix

| Ingredients | gms/Batch |
|---|---|
| Clonidine HCl | 85 |
| Sodium Polystyrene Sulfonate (Amberlite ® IRP-69) Cation Exchange Resin | 12750 |
| Povidone (Kollidon ® 30) | 1134 |
| Purified Water* | Qs* |

*Removed during processing

The clonidine-cation exchange resin matrix was prepared by first adding 80 L of purified water in a vessel following which clonidine HCl was added and dissolved by continuous mixing. Sodium polystyrene sulfonate resin (AMBERLITE® IRP-69) was dispersed with continuous mixing to form a slurry and the mixing continued for 60 minutes to permit formation of a complex between the clonidine and cation exchange resin. Water was removed from the slurry by filtration. Wet resin complex was rinsed twice using purified water. Wet resin complex was dried until the moisture content is about 10-20%. In a separate container povidone (Kollidon® 30) was dissolved in 2.834 kg of purified water (Povidone solution). The Povidone solution was then sprayed on to the wet clonidine-cation exchange resin complex with continuous mixing to form a uniform matrix. The clonidine-cation exchange resin matrix granules were dried until the moisture content was between 10-20%. The semi-dried granules were then passed through the CO-MILT™ fitted with a 40 mesh screen. The granules were further dried to a moisture content in the range of about 3% to about 7%. These dried granules were passed through the CO-MILT™ using a 40 mesh screen.

B. Ethylcellulose Coated Clonidine-Cation Exchange Resin Matrix

| Ingredients | gms/Batch |
|---|---|
| Clonidine-Cation Exchange Resin Matrix of Part A | 1000 |
| Aquacoat ™ ECD** | 1067** |
| Dibutyl Sebacate NF | 79 |
| Purified Water* | 221 |
| TOTAL | 1400 |

The coated clonidine-cation exchange resin matrix can be prepared as follows. The coating solution is prepared by mixing ethylcellulose aqueous dispersion (AQUACOATT™ ECD), dibutyl sebacate and purified water in a separate container. The coating solution is passed though a Seive No. 40 mesh screen. The coating process is performed in a VECTOR FLM-1™ fluid bed processor equipped with wurster column by applying 1369 g of coating solution to 1 kg of clonidine-cation exchange resin matrix, prepared according to Part A, to result in 40% weight gain. The ethylcellulose-coated clonidine-cation exchange resin matrix is then passed through a Seive No. 40 mesh screen and placed in the hot air oven at 60° C. for 2 hours. The coated clonidine-cation exchange resin matrix is again passed through Sieve No. 40 mesh screen.

All patents, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. An oral clonidine liquid suspension composition having a twenty-four hour extended release profile with a single plasma concentration peak following a single oral dose, said dosage unit comprising an aqueous liquid suspension base and a pharmaceutically effective amount of cured, barrier coated, clonidine-cation exchange resin complex-matrix particles, said cured barrier coating comprising polyvinylacetate and a plasticizer and being a cured, water-permeable, high tensile strength, water-insoluble, barrier coating having an elongation factor in the range of about 150% to 400%, wherein said cured barrier coating is over the matrix comprising a hydrophilic or hydrophobic matrix forming polymer and a complex comprising clonidine bound to a cationic exchange resin in a ratio of about 1:120 to about 1:180 clonidine to cation exchange resin,
   wherein said liquid suspension provides a mean plasma clonidine concentration in human patients of about 0.5 ng/mL at about 6 to about 10 hours following a single clonidine dose of about 0.2 mg.

2. The oral clonidine liquid suspension according to claim 1, wherein the cured barrier coating further comprises a stabilizer.

3. The oral clonidine liquid suspension according to claim 2, wherein the cured barrier coating is present in an amount of about 10% to 70% w/w of the clonidine-cation exchange resin complex-matrix prior to coating.

4. The oral clonidine liquid suspension according to claim 2, wherein the cured barrier coating is present in an amount of about 30 to 50% w/w of the clonidine-cation exchange resin complex-matrix prior to coating.

5. The oral clonidine liquid suspension according to claim 4, wherein the cured barrier coating is present in an amount of about 40% w/w of the clonidine-cation exchange resin complex-matrix prior to coating.

6. The oral clonidine liquid suspension according to claim 1, wherein clonidine to resin ratio is about 1:150.

7. The oral clonidine liquid suspension according to claim 1, wherein the plasma half-life of clonidine is 13.7 hours±3 hours.

8. The oral clonidine liquid suspension according to claim 1, wherein the barrier coating further comprises a a stabilizer and a surfactant.

9. The oral clonidine liquid suspension according to claim 1, wherein the plasticizer comprises about 2.5 to about 25% w/w of the barrier coating and is selected from the group consisting of triacetin, dibutyl sebacate, propylene glycol, polyethylene glycol, polyvinyl alcohol, triethyl citrate, acetyl triethyl citrate, acetyl tributyl citrate, tributyl citrate, and mixtures thereof.

10. The oral clonidine liquid suspension according to claim 8, wherein the stabilizer is polyvinylpyrrolidone and the surfactant is sodium lauryl sulfate.

11. The oral clonidine liquid suspension according to claim 10, wherein the polyvinyl pyrrolidone comprises about 5 to about 10% w/w of the barrier coating.

12. The oral clonidine liquid suspension according to claim 1, wherein the matrix forming polymer is a polymer or copolymer selected from the group consisting of a ethyl cellulose, cellulose acetate, acrylic based polymers or copolymers, cellulose phthalate, polyvinyl acetate and mixtures thereof.

13. The oral clonidine liquid suspension according to claim 12, wherein the matrix forming polymer is an acrylic based polymer or copolymer.

14. The oral clonidine liquid suspension according to claim 13, wherein the matrix forming polymer is a neutral copolymer comprising ethyl acrylate and methyl methacrylate.

15. The oral clonidine liquid suspension according to claim 1, wherein the dosage unit comprises a multiplicity of coated clonidine-cation exchange resin complex-matrix particles, said coated clonidine-cation exchange resin complex-matrix particles having an average particle size in the range of 50 to 300 microns.

16. A method for delivering an effective amount of clonidine for a twenty-four hour period which provides a single peak plasma concentration, the method comprising administering to a subject a single oral clonidine liquid suspension according to claim 1 in the evening.

17. The oral clonidine liquid suspension according to claim 1 which comprises a multiplicity of coated clonidine-cation exchange resin complex-matrix particles, said coated matrix particles having an average particle size in the range of about 20 microns to about 200 microns.

18. The oral clonidine liquid suspension according to claim 1, which provides a mean plasma concentration for clonidine in human patients of about 0.49 (±0.09) ng/mL at 7.8 hours (±1.7 hours) following a single clonidine dose of about 0.2 mg.

19. The oral clonidine liquid suspension according to claim 1, wherein the plasma half-life of clonidine following a single dose of the composition is about 10 to about 18 hours.

20. The oral liquid suspension according to claim 19, wherein the plasma half-life of clonidine is 13.7 hours±3 hours.

21. The oral liquid suspension according to claim 1, wherein the cured barrier coating is present in an amount of about 30% by weight to about 50% by weight of the clonidine-cation exchange resin complex-matrix prior to coating thereof.

22. The oral liquid suspension according to claim 1, wherein the matrix forming polymer is polyvinylpyrrolidone.

23. The oral liquid suspension according to claim 1, wherein the cured barrier coating layer comprises about 70 to 90% by weight polyvinylacetate polymer and about 2.5 to about 10% by weight plasticizer.

24. The oral liquid suspension according to claim 1, wherein the plasticizer is triacetin.

25. An oral clonidine tablet having a twenty-four hour extended release profile with a single plasma concentration peak following a single oral dose, said tablet comprising pharmaceutically acceptable excipients and a pharmaceutically effective amount of cured, barrier coated, clonidine-cation exchange resin complex-matrix particles compressed into a tablet form, said cured barrier coating being a cured, water-permeable, high tensile strength, water-insoluble, barrier coating having an elongation factor in the range of about 150% to 400% and comprising polyvinylacetate and a plasticizer, wherein said cured barrier coating is over the matrix comprising a hydrophilic or hydrophobic matrix forming polymer and a complex comprising clonidine bound to a cationic exchange resin in a ratio of about 1:120 to about 1:180 clonidine to cation exchange resin, wherein said tablet provides a mean plasma concentration for clonidine in human patients of about 0.5 ng/mL at about 6 to about 10 hours following a single clonidine dose of about 0.2 mg.

26. The oral clonidine tablet according to claim 25, which provides a mean plasma concentration for clonidine in human patients of about 0.49 (±0.09) ng/mL at 7.8 hours (±1.7 hours) following a single clonidine dose of about 0.2 mg.

27. The oral clonidine tablet according to claim 25, wherein the plasma half-life of clonidine following a single dose of the composition of is about 10 to about 18 hours.

28. The oral clonidine tablet according to claim 25, wherein the plasma half-life of clonidine is 13.7 hours±3 hours.

* * * * *